United States Patent [19]

King et al.

[11] 4,028,325

[45] June 7, 1977

[54] COMPOSITE DENTAL MATERIAL AND METHOD OF PREPARING SAME

[76] Inventors: Alan G. King, 827 Chenook Trail, Macedonia, Ohio 44056; Leon Levine, 94 Brewster Road, West Hartford, Conn. 06117

[22] Filed: Mar. 7, 1975

[21] Appl. No.: 556,397

Related U.S. Application Data

[63] Continuation-in-part of Ser. No. 279,033, Aug. 9, 1972, abandoned.

[52] U.S. Cl. .................. 260/42.15; 32/12; 32/15; 32/59; 260/42.28; 260/42.52; 260/998.11; 264/19
[51] Int. Cl.² ...................... C08K 9/06; C08K 3/22
[58] Field of Search ....... 260/998.11, 42.15, 42.28, 260/42.52; 32/8, 12, 15; 106/35

[56] References Cited

UNITED STATES PATENTS

| | | | |
|---|---|---|---|
| 3,052,982 | 9/1962 | Weinstein et al. | 32/8 |
| 3,066,112 | 11/1962 | Bowen | 260/998.11 |
| 3,423,828 | 1/1969 | Halpern et al. | 32/8 |
| 3,751,399 | 8/1973 | Lee et al. | 260/998.11 |
| 3,801,344 | 4/1974 | Dietz | 106/35 |

*Primary Examiner*—James H. Derrington
*Attorney, Agent, or Firm*—Paul Maleson; Morton J. Rosenberg

[57] ABSTRACT

A composite material and method of preparing same for use in prosthetic dentistry. The composition includes silica glass containing between about 8.0–30% on a weight basis of alkaline earth metal oxides and/or alkali metal oxides in solution selected from the group consisting of calcium oxide, magnesium oxide, sodium oxide, potassium, and lithium oxide. In one form of the invention, a methacrylate resin is coupled to the silica glass by a silane mixture. The invention includes the method of forming the composite material through both a cold curing system and a heat cured system into a composite veneering and tooth material which is useful in forming crowns and other dental restorations as well as artificial teeth requiring aesthetic appearance of normal dentition. The finally formed dental material shows a high hardness factor in combination with a high wear resistance. The composite material has the capability of being highly polishable and provides for low toxicity as well as a low index which allows optical matching of the composite material to naturally formed teeth.

18 Claims, No Drawings

COMPOSITE DENTAL MATERIAL AND METHOD OF PREPARING SAME

CROSS REFERENCES TO RELATED APPLICATIONS

This application is a continuation-in-part application of patent application Ser. No. 279,033 filed Aug. 9, 1972, now abandoned.

BACKGROUND OF THE INVENTION

1. Field of Art

The invention relates to the field of materials used for dental applications. In particular this invention pertains to a composite material for use as artificial teeth as well as crown and bridge veneer having low toxicity and optical index. More in particular this invention relates to a dental material mixture and method of preparing same which includes glass containing predetermined amounts of certain alkali and/or alkaline earth elements oxides having high wear resistance.

2. Prior Art

Dental materials used for veneers are well known in the art. However, some of the prior veneering materials used have a plastic base. Although plastic has been found to be easy to repair and handle, the low wear resistance characteristics provide problems in maintaining the plastic material in use for a prolonged period of time.

Other materials used for veneering include porcelain which has the advantage of durability. However, such porcelain materials are found to be brittle and difficult to repair when damaged.

In U.S. Pat. No. 3,066,112 Bowen describes the use of fused silica coupled to a resin with vinyl silane. The resin is an adduct of bisphenol A with glycidyl methacrylate or glycidyl acrylate. Chemically, the methacrylate resin is isopropylidenebis [p-phenyleneoxy (2-hydroxy-trimethylene)] dimethacrylate commonly called BisGMA. The material is described as useful in dental fillings and uses peroxide as a catalyst and an N,N-disubstituted aromatic amine as accelerator, but does not incorporate the use of alkali and/or alkaline earth elements as in the instant invention.

In U.S. Pat. Nos. 3,179,623; 3,194,783; and 3,194,784 Bowen further describes a variety of resin derivities using fused silica and useful for filling cavities in teeth. Bowen in U.S. Pat. No. 3,539,526 describes a dental filling material including barium containing glasses. However, it has been found that barium, as well as strontium, cesium, rubidium and heavier elements have a pronounced disadvantage in their toxicity as well as high index of refraction. This high toxicity causes the barium containing glass to interact with body fluids in the cavity and acts as irritants to tissues. The high index causes excessive opaqueness and does not allow for easily matching the filling material with naturally formed teeth. This may not be a decided disadvantage when used as a dental filling material as is described in the Bowen reference but is highly disadvantageous in the instant invention when the composite material is used for artificial teeth as well as crown and bridge veneer.

Chang describes a dental composite in U.S. Pat. No. 3,452,437 using glass spheres and fibers. This material is described as a tooth filling material but no mention is made as to glass containing alkali and/or alkaline earth metals of the subject invention.

Veneers being applied to crowns on anterior teeth in the dental laboratory is known in the art. Cornell U.S. Pat. Nos. 3,265,202 and 3,488,846 describes a resin system which is heat cured to produce a plastic veneer. However, the material described does not utilize a ceramic filler. Although referred to as a composite material in the patents such is not usually considered a composite material in the dental materials sense since it lacks ceramic fillers.

Lee in U.S. Pat. Nos. 3,539,533 describes a composite useful for filling teeth where the filler is quartz and the resins are BisGMA and bisphenol A dimethacrylate. In this reference, it is not believed that Lee provides for a silica glass containing predetermined percentages of alkaline and/or alkali metal oxides for use as artificial teeth or crown or bridge veneer.

In each of the above cited patents the application of composites is limited to filling cavities. Materials made according to each of the teachings of the cited references are not suitable for veneer restorations, as none of them can be polished to a high gloss or luster. The invention described herein has the unique capacity to take on a high gloss and reflective polish, and therefore extends the utilization of composite materials into this area of prosthetic dentistry. The material can be adapted to a cold cure or heat cure system to fill a variety of technique requirements. Additionally, the inventive composite has the convenience and ease of handling of plastics, and approaches the durability of porcelain.

SUMMARY OF THE INVENTION

A composite material for use in dentistry. The material principally comprises a silica glass containing on a weight basis of between about 8.0–30.0% of alkaline earth metal oxides and alkali oxides in solution where the alkaline earth and alkali metal oxides are selected from the group consisting of calcium oxide, magnesium oxide, sodium oxide, potassium oxide, and lithium oxide. A methacrylate resin is coupled to the silica glass by a silane mixture.

An object of the instant invention is to provide a veneering composite material which is of low cost to manufacture.

Another object of the present invention is to provide a veneering composite material which may be easily applied through known techniques in the dental industry.

A still further object of the instant invention is to provide a veneering composite material which has improved durability over pre-existing materials used for veneering.

Another object of this invention is to provide a high strength, durable and low modulus of elasticity material for use in artificial teeth.

Another object of the subject invention is to provide a composite system which is chemically cured at room temperatures making it suitable for chairside usage.

Another object of the subject invention is to provide a composite material system adapted to heat curing suitable for laboratory procedures in forming aesthetically acceptable dental veneers.

A still further object of the instant invention is to provide a material suitable for chairside restorations of lost dentition.

Another object of the subject invention is to provide a dental material which can be highly polished.

DESCRIPTION OF THE PREFERRED EMBODIMENTS

Referring now to the invention, there is hereinafter described a dental material composite and methods of preparing same for use in making crowns, bridge veneers, and artificial teeth. In broad concept, the composite consists of a dispersion of glass particles in a resin matrix. A silane coupling agent is used to promote bonding between the two phases. The glass particles contain in solution a predetermined weight percentage of predetermined alkaline earth metal oxides and/or alkali metal oxides forming a glass mixture. The metal atoms are generally radomally distributed throughout the glass in solution and are bonded to oxygen atoms in the random glass network. The glass mixture is generally added to a methacrylate resin and coupled by a silane. Other forms of the material composition provide for the addition of dimethacrylate resin solution, methyl methacrylate resin solution and dimethacrylate singularly and in combination as will be shown in the following examples.

One form of the composite material principally comprises silica glass containing on a weight basis of between about 0.0% 18.0%, preferably 7.0–13.0% of alkaline earth metal oxides in solution where the alkaline earth metal oxides are selected from the group consisting of calcium oxide and magnesium oxide. The silica glass is then coupled to a methacrylate resin by a silane mixture. Useful percentages of the calcium oxide on a weight basis when taken with respect to the silica was found to be between approximately 0.0–13.0%. Magnesium oxide was found to be optimally useful on a weight basis of between approximately 0.0–5.0% of the silica glass.

Another composite material found to be useful in making crowns, bridge veneers and artificial teeth included a silica glass containing on a weight basis of between about 1.0–20.0%, preferably 14.0–18.0%, of alkali metal oxides in solution where the alkali metal oxides were selected from the group consisting of sodium oxide, potassium oxide and lithium oxide. The silica glass was coupled to a methacrylate resin by a silane mixture. Useful weight percentages taken with respect to the silica glass for sodium oxide was found to be between approximately 0.0– 18.5%, for the potassium oxide to be between approximately 0.0% 11.0%, and for the lithium oxide to be between approximately 0.0–8.0%.

Combinations of the alkaline earth as well as alkali metal oxides provided a useful composite material principally comprising silica glass containing on a weight basis of between approximately 8.0–30.0%, preferably 10.0–27.0% of metal oxides in solution where the metal oxides were selected from the group consisting of sodium oxide, potassium oxide, lithium oxide, calcium oxide, and magnesium oxide. In this form a methacrylate resin was coupled to the silica glass by a silane mixture. As previously described, the metal oxide weight percentages of the silica glass included, between approximately 0.5–13.0% of calcium oxide, between approximately 0.0–5.0% of magnesium oxide, between approximately 0.0–18.5% of sodium oxide, between approximately 0.0–11.0% potassium oxide, and between approximately 0.0–8.0% of lithium oxide.

As the aforementioned metal oxides were increased by weight percentage of the silica glass it was found that the material became more soluble and tended to leach out and loose substance. When the weight percentage of the metal oxides approached 30.0% by weight of the silica glass it was found that the material became excessively soluble and lost sufficient substance such that the composite material was deemed to be in a nonuseful range. As the weight percentage of the metal oxides when taken with respect to the silica glass was lowered it was found that the glass mixture became viscous and hard to melt. When the weight percentage of the metal oxides when taken with respect to the silica glass was lowered below 8.0% it was found that the viscosity of the glass mixture became too high for easy workability. In general, it was found that when the metal oxide weight percentages remained between 10.0–27.0% that the composite material formed provided optimum properties as has been hereinbefore described. Additionally, the invention concept material has now discovered that the use of predetermined glass fillers coupled with silanes in a methacrylate resin vehicle produces a truly polishable composite which increases the utility of this system material to include veneering.

Thus, the invention as is herein detailed is further directed to the applying of the resulting dental materials to a heat curing process whereby bridge veneers and artificial teeth may be constructed under laboratory conditions. The resulting dental material is also directed to the application of a cold curing process whereby dental restorations are made in a chairside environment.

The combination of materials results in a dental composition having high strength characteristics, a high degree of hardness, and the capacity to be highly polished. The material may be pigmented and adjusted to a wide variety of translucency by using glass particulates having varying indices of refraction.

The following paragraphs detail various embodiments of the basic composite material composition used in both the cold cure system and heat cure system as well as their use in the formation of artificial teeth.

In following paragraphs eight examples are shown relating to a cold curing system, heat curing system, and method of making artificial teeth. For each of these examples, varying amounts of alkali and alkaline earth metal oxides were incorporated in solution with silica glass. Table I, as shown below provides for ten runs which were made for each example case. These runs provide for typical combinations of alkali and alkaline earth metal oxides which were found useful in each of the system described. The weight percentages of the metal oxides shown in Table 1 are taken with respect to the silica glass with which they are combined in solution. Rubidium, cesium, strontium, barium, and heavier elements were not used due to their toxicity as well as high index which made the material excessively opaque and did not allow matching with naturally formed teeth. In particular, barium containing glasses were found to be disadvantageous in composites as being potentially toxic as well as imparting to a catalyst paste the property of having a poor shelf life.

TABLE I

| | ALKALI & ALKALINE EARTH METAL OXIDES (% weight) | | | | | TOTAL METAL OXIDE CONTENT |
|---|---|---|---|---|---|---|
| | $Na_2O$ | $K_2O$ | $Li_2O$ | CaO | MgO | |
| n 1 | 14 | | 13 | | | 27 |

TABLE I-continued

ALKALI & ALKALINE EARTH METAL OXIDES (% weight)

|       | Na$_2$O | K$_2$O | Li$_2$O | CaO | MgO | TOTAL METAL OXIDE CONTENT |
|-------|---------|--------|---------|-----|-----|---------------------------|
| n 2   | 18½     |        |         | 7   |     | 25½                       |
| n 3   | 17      |        |         | 5   | 5   | 27                        |
| n 4   | 5       | 8      |         | 10  |     | 23                        |
| n 5   | 9       | 11     |         | 5   |     | 25                        |
| n 6   | 14      | 0.5    |         |     | 4   | 18½                       |
| n 7*  |         |        | 8       |     |     | 8                         |
| n 8   | 17      | 2      |         | 6   | 5   | 30                        |
| n 9** |         |        |         |     | 10  | 10                        |
| n 10*** | 1     |        |         | 8   | 7   | 16                        |

*plus 27% Al$_2$O$_3$
**plus 25% Al$_2$O$_3$
***plus 5% B$_2$O$_3$

COLD CURE SYSTEM

The cold cure composite is formulated either as a liquid-powder system or a two paste accelerator, catalyst system. The liquid of the liquid-powder system and both the catalyst and accelerator paste contain BisGMA diluted to a useful viscosity with a methacrylate monomer. The monomers are methyl methacrylate, ethylene glycol dimethacrylate, diethylene glycol dimethacrylate, triethylene glycol dimethacrylate, tetraethylene glycol dimethacrylate or polyethylene glycol dimethacrylate.

The preferred compositions contain BisGMA in a range of 50 to 75% by weight of the total monomer composition and a low vapor pressure dimethacrylate in a range of 25 to 50% by weight of the combination of BisGMA and dimethacrylate.

It has been found that the dimethacrylates when used alone yield an effective veneer composition. Also, solutions of methlemthacrylate in the weight range of 25 to 50% of total monomer composition and dimethacrylates in the weight range of 50 to 75% have been used. The polymerization shrinkage is greater in the non-BisGMA formulations but fall within acceptable ranges.

An N,N-disubstituted aromatic amine was used as the accelerator. Examples of amines which are used included, N,N-diemthylaniline, dimethyl-p-toluidine, N, N-dimethyl, 3, 5-xylidine, N-phenyldiethanol amine, N, N-diethyl aniline, N, N-diethyl p-toluidine and p-tolyliminodiethanol. Other amines may be found to be suitable and the aforementioned are used as examples and are not meant to limit the scope of the invention.

It has been found that the cold cure system can be initiated at room temperature (approximately 21° C.) and reach an adequate exotherm to give a sufficient cure. It is to be understood that while the cold cure system can be used chairside, it can be used in a dental laboratory with the cure starting at room temperature in a pressure pot to prevent voids.

Benzoyl peroxide is the preferred catalyst. Polymerization inhibitors used in the formulation are 2, 6-ditertrary butyl-p-cresol, hydroquinone, hydroquinone-methyl ether, p-t-butyl catechol, t-butyl hydroquinone. The ceramic filler is a finely divided silica based glass containing alkaline earth and/or alkali metals.

EXAMPLE I

EXAMPLE I

| Resin Formulation | |
|---|---|
| BisGMA | 67 parts |
| Ethylene glycol dimethacrylate | 33 parts |
| N, N, 3, 5-tetramethylaniline | 1.50 parts |
| 2, 6-Di-Tert butyl-p-cresol (BHT) | 0.19 parts |
| Powder Formulation | |
| Alkali-alkaline earth containing silica glass | 100 parts |
| Silane | 0.20 parts |
| Benzoyl Peroxide | 0.50 parts |
| Pigments are required | |

In overall composition, approximately 10 gram of powder was mixed with about 0.21 ml. of liquid. In this example, to form the powder, a slurry in acetone was prepared from the constituents and dried at 50° C. until the solvent was removed. Other conventional mixing techniques could have been instituted to accomplish the same result.

The amounts of Benzoyl peroxide, amine, and BHT can be varied to produce a variety of materials with different working times, and set times. The composition described in EXAMPLE I has a working time of one minute and 45 seconds, and a set time of three minutes. After a 10 minute cure at 37° C., the material can be readily polished by smoothing with a wet 600 grit silicon carbide abrasive paper, and a one micron alumina powder on a felt or suede buff moistened with water.

In the instant example a series of runs were made using various constituents of both alkali metals and alkaline earth metals singularly and in combination within the silica glass as shown in TABLE I.

EXAMPLE II

EXAMPLE II

| Accelerator Paste | |
|---|---|
| Alkali-Alkaline earth containing silica glass, silane added | 100 parts |
| BisBMA resin monomer | 13.70 parts |
| Tetraethylene glycol dimethacrylate | 6.85 parts |
| N, N, 3, 5-tetramethylaniline | 0.20 parts |
| BHT | 0.25 parts |
| Catalyst Paste | |
| Alkali-alkaline earth containing silica glass, silane treated | 100 parts |
| Benzoyl peroxide | 1.0 parts |
| BisGMA resin | 13.70 parts |
| Tetraethylene glycol dimethacrylate | 6.85 parts |
| BHT | 0.25 parts |
| Pigment as required | |

In order to form the composite material in a manner convenient for use in a dental office, a two paste system was instituted as shown in EXAMPLE II. In this example an accelerator paste and a catalyst paste were formed by using the shown constituents. Equal amounts of each paste are mixed and used to form the veneer. A number of other monomers and amines can be substituted for those shown in this example.

EXAMPLE III

EXAMPLE III

| Resin Formulation | |
|---|---|
| Methyl methacrylate | 20 parts |
| Ethyleneglycol dimethacrylate | 48 parts |
| N, N, 3, 5-tetramethylaniline | 0.6 parts |
| BHT | 0.033 parts |
| Pigment as required | |

In this example a non-BisGMA containing resin was used and found useful for veneer restorations. This liquid (resin formulation) was mixed with the Powder Formulation shown in EXAMPLE I. In overall composition, approximately 0.24 ml. of liquid was mixed with approximately 1.0 gram of powder. The resulting paste was applied to form a veneer. The two paste system was formulated using the above listed monomers, although other runs were instituted using combinations of monomers previously described and resulting in acceptable veneers.

Useful ranges of composition included:

| | | | | |
|---|---|---|---|---|
| Benzoyl Peroxide | 0.3 | – | 2.0 | parts |
| Amine | 0.1 | – | 1.5 | parts |
| BHT | 0.03 | – | 0.3 | parts |

The formulation should be adjusted so as to produce a working time between 60 and 200 seconds. Different commercial resins produce composite materials with different set times. Specific formulations are adjusted for the set time desired for each resin.

The powder and liquid are mixed in the approximate proportions of 1 gram of powder to 0.2 ml. of liquid. The amounts are variable depending on the specific gravity of the glass and the viscosity desired.

The cold cure system is useful for repairing worn or broken veneers on pre-existing restorations and in general as a chairside procedure. After mixing the two ingredients, the paste is applied to the prepared surface requiring the veneer. An excess of material is applied. A translucent incisal veneer is applied to the incisal portion of the restoration. This composition utilizes a glass with an index of refraction close to that of the resin. After approximately 10 minutes, the veneer has set to a hard mass and is shaped with cemented carbide or diamond burs. It is also finished with abrasive discs where applicable, smoothed with a 600 grit silicon carbide disc, and polished with a finely divided alumina polishing powder on a moistened buff such as felt or suede material.

HEAT CURE SYSTEM

For laboratory formulation of a form of the composite dental material, a heat cure system or process is used. This type of procedure is for the making of veneers. Since curing is done at an elevated temperature, this procedure is not applicable to chairside application. In general, the material used may be in the form of a powder and liquid which is mixed to form a paste or as a premixed paste. Monomers and polymerization inhibitors used in the heat curing process are the same as that used in cold curing. One difference in the formulation of the heat curing material is that no amine is used as was included in the cold curing system. Other free radical catalysts as azocatalysts, hydroperoxides as well as other peroxides such as lauoryl peroxide, or t-butyl peroxymaleic acid may be used. As important feature is that a half life at 212° F. of the catalyst used be that of lauoryl peroxide or greater.

EXAMPLES IV and V shown below provide basically the same constituents with the exception that BisGMA and tetraethylene glycol dimethacrylate are used in EXAMPLE IV and ethyleneglycol dimethacrylate in combination with methyl methacrylate are used in EXAMPLE V. As is the case in all examples, the number of parts of each contituent is taken as a function of weight.

EXAMPLE IV

| | |
|---|---|
| Alkali-Alkaline Earth Containing Silica glass, silane treated | 100 parts |
| BisGMA resin monomer | 13.70 parts |
| Tetraethylene Glycol Dimethacrylate | 6.85 parts |
| 2, 6-Di-Tertbutyl-p-cresol (BHT) | 0.037 parts |
| Benzoyl Peroxide | 0.51 parts |

EXAMPLE V

| | |
|---|---|
| Alkali-Alkaline Earth Containing Silica glass, silane treated | 100 parts |
| Ethyleneglycol dimethacrylate | 13.70 parts |
| 2, 6 - Di-t-butyl-p-cresol | 0.037 parts |
| Benzoyl Peroxide | 0.50 parts |
| Methyl Methacrylate | 6.85 parts |
| Pigments as required | |

In each of the above examples, the constituents were mixed in accordance with the method previously described, or by any well known mixing technique. The particular mixing technique not being critical to the invention concept except that such should yield a paste which is substantially homogeneous in nature. The paste is applied to a crown which has previously been coated with an opaquer. The paste is cured in hot air stream, and the incisal paste is then applied to the incisal tip of the restoration, and cured. The veneer is heated to approximately 100° C. for about ¼ hours in an oven to obtain the final set. The restoration is now shaped and polished. An important concept in the invention is the use of a glass containing hydratable ions in sufficient amount to enhance the silane bond, as well as the use preferentially of a dimethacrylate monomer, as the matrix. Strong and polishable materials were obtained using lithium, and soda-lime crown glasses. The essential constituent is the presence of the alkali or alkaline earth element. Composite compositions containing similar formulations but with a fused silica or quartz filler have compressive strengths between 10 and 20% lower, and cannot be polished by any known technique available in dentistry. Optimum particle size of the glass is minus 325 mesh.

The Knoop microhardness of the subject invention is 115 units, as compared to 50 units of a material using a fused silica filler. TABLE II summarizes physical properties of several materials.

TABLE II

| Property | Present Invention | Fused Silica Filler | Quartz Filler |
|---|---|---|---|
| Compressive Strength, psi | 41,500 | 32,000 | 28,000 |
| Tensile Strength, psi | 5,650 | 6,200 | 4,400 |
| Transverse Strength, psi | 12,400 | — | 14,200 |
| MicroHardness Knoop (100g) | 115 | 50 | |
| Rockwell H | off scale | — | 100 |
| Rockwell A | 44.7 | 38.7 | |

While the tensile and transverse strength are comparable with other materials, these data show that a considerable increase is achieved in compressive strength and hardness. This will increase the durability to wear processes over pre-existing materials.

Polishing is achieved with a 600 grit silicon carbide paper with a stiffened backing to smooth the restoration, and a suede or felt facing adhered to a plastic or paper backing in the form of a disc. Finely divided alumina is used on the felt as a polishing material, but other hard, finely divided abrasives could also be used. The optimum particle size of the polishing powder is between 2.0 and 0.2 microns. A powder with a median particle size of 2½ microns was found not to produce a good polish, and materials finer than 0.2 microns polish too slowly to be practical.

ARTIFICIAL TEETH

In general, the overall composition of the composite material used in making up artificial teeth is very similar to that of the heat cured veneer. As applicable to the Examples shown below, a suitable transfer or compression mold is enameled with a material of increased translucency. After this the body portion of the tooth, pigmented to an appropriate color was inserted. In each case, the material is heat cured in the mold, removed and finished. The ability of the final artificial tooth to be polished is of great importance in finishing operations during manufacture, and grinding as well as during fitting of the tooth to fit a particular denture. The lack of polishability, as previously described, has prevented the use of composite materials for artificial teeth in prior tooth construction.

Basic constituents in the composite material for artificial tooth construction are shown in the following examples:

EXAMPLE VI

EXAMPLE VI

| | |
|---|---|
| Alkali-Alkaline Earth Containing Glass, Silane Treated | 100 parts |
| BisGMA resin | 13.7 parts |
| TetraEGDM | 6.85 parts |
| Benzoyl Peroxide | 0.51 parts |
| Pigments as required | |

EXAMPLE VII

EXAMPLE VII

| | |
|---|---|
| Alkali-Alkaline Earth Containing Silica Glass, Silane Treated | 100 parts |
| Ethyleneglycol Dimethacrylate | 13.70 parts |
| Methyl Methacrylate | 6.85 parts |
| Benzoyl Peroxide | 0.5 parts |
| Pigments as required | |

EXAMPLE VIII

EXAMPLE VIII

| | |
|---|---|
| Alkali-Alkaline Earth Containing Silica Glass, Silane Treated | 100 parts |
| BisGMA Resin | 13.70 parts |
| Methyl Methacrylate | 6.85 parts |
| Benzoyl Peroxide | 0.5 parts |
| Pigments as required | |

In the above examples the constituents or ingredients were mixed to form a stiff paste. A three piece compression mold is used to form the teeth. The pigmented body or gingival portion of the paste is inserted into the bottom half of the mold. The gingival or body portion is shaped by using the second mold part. The body portion with shaper is placed on a hot press for 3 minutes at 210° F. and partially cured. After cooling the body shaper part of the mold is removed and the pigmented enamel paste is placed over the cured body paste. The top of the mold is placed on and the mold is subjected to pressure to fill the cavities and form the tooth shape. Excess paste is removed and the mold, now containing the materials, shaped into a complete tooth form. Curing was accomplished at 350° F. and about 8000 psi for 3 minutes. Curing was accomplished by conventional techniques well known in the art. After cooling, the teeth were removed from the mold.

A portion of both the mesial and distal sides of an anterior tooth were removed by grinding. The surfaces had a dull finish. The full durface were polished using the methods already described to a high gloss surface. The ability to polish surfaces which have been ground away and are dull is necessary for use of the composite teeth in a dental laboratory.

In all cases described, the glass portion of the total composite material was approximately 80% by weight. Soda-lime crown glass was found to work well for these applications. It was found that such glass could be produced at costs similar to those for dental porcelain raw materials.

Previously artificial teeth have been made from either acrylic plastic or porcelain. Each of these materials has previously described limitations. Plastic has a Knoop microhardness below 10 resulting in a material which is soft and can suffer a high rate of attrition in abrasive conditions. Acrylic plastics have the marked advantage however of being bondable to the denture base during curing of the denture, and of having a low modulus which prevents the dentures from clicking during conversation. Porcelain teeth are brittle with transverse strengths commonly below 10,000 psi and cannot be bonded to the denture base. This necessitates the costly insertion of precious metal containing pins and retainers, or expensive molding of other mechanical retention devices. Porcelains have a modulus between 10 and 20 million psi, and the teeth tend to "click" during conversation.

The subject invention incorporate the better aspects of both materials. The composite is strong as shown in TABLE II, and it is bondable to the denture base in a manner similar to that used with plastic, as well as having a low modulus of 1.9 million psi which is 1/5 to 1/10th that of porcelain. Our invention composite material is also much harder than plastics. Typical Knoop microhardness for acrylic teeth are less than ten units, as compared to 115 for our invention. This gives the composite material a resistance to abrasion and loss of surface polish ten times that of plastic, as determined by brushing tests.

What is claimed is:

1. A composite material for use in dentistry principally comprising: (A) silica glass composition consisting of on a weight basis of between about 7.0–18.0% of alkaline earth metal oxides in solution wherein said alkaline earth metal oxides are selected from the group consisting of calcium oxide, and magnesium oxide; and, (B) a methacrylate resin coupled to said silica glass by a silane mixture, said composite material including on a weight basis approximately 100 parts of said silica glass composition to between approximately 13.5 to 65 parts of said methacrylate resin.

2. The composite material as recited in claim 1 wherein said calcium oxide on a weight basis is between approximately 0.0– 15.05% of said silica glass.

3. The composite material as recited in claim 1 wherein said magnesium oxide on a weight basis is between approximately 0.0–5.0% of said silica glass.

4. The composite material as recited in claim 1 wherein said alkaline earth metal oxides on a weight basis is between approximately 7.0–13.0% of said silica glass.

5. The composite material as recited in claim 1 wherein said methacrylate resin is BisGMA.

6. The composite material as recited in claim 1 wherein said composition (B) is a resin solution composed of methyl methacrylate and dimethacrylate.

7. A composite material for use in dentistry principally comprising: (A) silica glass composition consisting of on a weight basis of between about 1.0–20.0% of alkali metal oxides in solution wherein said alkali metal oxides are selected from the group consisting of sodium oxide, potassium oxide and lithium oxide; and, (B) a methacrylate resin coupled to said silica glass by a silane mixture, said composite material including on a weight basis approximately 100 parts of said silica glass composition to between approximately 13.5 to 65 parts of said methacrylate resin.

8. The composite material as recited in claim 7 wherein said sodium oxide on a weight basis is between approximately 14.0 18.0% of said silica glass.

9. The composite material as recited in claim 7 wherein said potassium oxide on a weight basis is between approximately 0.0–11.0% of said silica glass.

10. The composite material as recited in claim 7 wherein said lithium oxide on a weight basis is between approximately 0.0– 8.0% of said silica glass.

11. The composite material as recited in claim 7 wherein said methacrylate resin is BisGMA.

12. The composite material as recited in claim 7 wherein said composition (B) is a resin solution composed of methyl methacrylate and dimethacrylate.

13. The composite material as recited in claim 7 wherein said alkali metal oxides on a weight basis is between approximately 10.0–27.0% of said silica glass.

14. A composite material for use in dentistry principally comprising: (A) silica glass composition consisting of on a weight basis of between approximately 8.0–30.0% of metal oxides in solution wherein said metal oxides are selected from the group consisting of sodium oxide, potassium oxide, lithium oxide, calcium oxide, and magnesium oxide; and, (B) a methacrylate resin coupled to said silica glass by a silane mixture, said composite material including on a weight basis approximately 100 parts of said silica glass composition to between approximately 13.5 to 65 parts of said methacrylate resin.

15. The composite material as recited in claim 14 wherein said methacrylate resin is BisGMA.

16. The composite material as recited in claim 15 including (D) a dimethacrylate resin solution.

17. The composite material as recited in claim 15 including (D) a methyl methacrylate resin solution.

18. The composite material as recited in claim 14 wherein said metal oxides on a weight basis is between approximately 10.0– 27.0% of said silica glass.

* * * * *